United States Patent [19]

Lowe et al.

[11] 4,092,341

[45] May 30, 1978

[54] PROCESS OF MAKING AN OIL SOLUTION OF ZINC DIHYDROCARBYLDITHIOPHOSPHATES

[75] Inventors: Alexander George Lowe, Reading; Philip Edward Derbyshire, Little Sandhurst, near Camberley, both of England; Andrew George Papay, Manchester, Mo.

[73] Assignee: Edwin Cooper and Company Limited, Bracknell, England

[21] Appl. No.: 768,143

[22] Filed: Feb. 14, 1977

[30] Foreign Application Priority Data

Feb. 27, 1976 United Kingdom ............... 7853/76

[51] Int. Cl.$^2$ ............................................... C07F 3/06
[52] U.S. Cl. ......................... 260/429.9; 252/32.7 E
[58] Field of Search ............... 260/429.9; 252/32.7 E

[56] References Cited

U.S. PATENT DOCUMENTS

| | | | |
|---|---|---|---|
| 2,689,220 | 9/1954 | Mulvany | 252/32.7 E |
| 3,086,939 | 4/1963 | Tichelaar | 252/32.7 E |
| 3,277,003 | 10/1966 | Gragson | 252/32.7 E |
| 3,562,306 | 2/1971 | Blaha et al. | 260/429.9 |

*Primary Examiner*—Helen M. S. Sneed
*Attorney, Agent, or Firm*—Donald L. Johnson; Robert A. Linn; Joseph D. Odenweller

[57] ABSTRACT

Zinc dihydrocarbyldithiophosphates are made by the reaction of zinc oxide with dihydrocarbyldithiophosphoric acid in the presence of mineral oil which has been reacted with nitrogen dioxide. The nitrogen dioxide treatment alters the oil such that it promotes the zinc oxide reaction. The process is especially adapted for making zinc dialkaryldithiophosphates useful as lubricating oil additives.

4 Claims, No Drawings

PROCESS OF MAKING AN OIL SOLUTION OF ZINC DIHYDROCARBYLDITHIOPHOSPHATES

BACKGROUND

Zinc dihydrocarbyldithiophosphates are well-known lubricating oil additives. When added to oil in small amounts they impart both antioxidant and antiwear properties to the oil. The major use for such oils is in crankcase oils for internal combustion engines.

Zinc dihydrocarbyldithiophosphates are made by the reaction of an alcohol or phenol with phosphorus pentasulfide to form the corresponding O, O-dihydrocarbyldithiophosphoric acid which is then reacted with zinc oxide to form zinc dihydrocarbyldithiophosphate. The reaction with zinc oxide proceeds quite well with dialkyldithiophosphoric acids, but with diaryldithiophosphoric acids the reaction with zinc oxide is much slower and it is very difficult to obtain a "sweet" product — i.e., a product having a pH over about 5.0. In Blaha, British Pat. No. 1,289,199 (U.S. Pat. No. 3,562,306), there is provided an improvement in the process whereby zinc nitrate, chloride or sulfate are added as a reaction promoter.

SUMMARY

According to the present invention, the reaction of zinc oxide with dihydrocarbyldithiophosphoric acid is promoted by conducting it in a mineral oil which has been reacted with nitrogen dioxide ($NO_2$).

DESCRIPTION OF THE PREFERRED EMBODIMENTS

A preferred embodiment of the present invention is an improvement in the process of making zinc dihydrocarbyldithiophosphates by reacting zinc oxide with dihydrocarbyldithiophosphoric acids. In the improved process the reaction is conducted in a mineral oil which has been reacted with $NO_2$.

The preparation of the dithiophosphoric acid is well known and can be represented by the following equation:

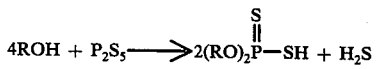

$$4ROH + P_2S_5 \longrightarrow 2(RO)_2\overset{S}{\underset{\|}{P}}-SH + H_2S$$

wherein R represents the same or different hydrocarbyl radicals. In the preparation of the acid any alkanol or phenol can be used provided that if oil solubility is to be imparted to the product at least one of the alkanols contains an aliphatic group of at least 5 carbon atoms. Examples of suitable alkanols are isopropanol, n-butanol, isobutanol, amyl alcohol, n-hexanol, cyclohexanol, 2-ethyl hexanol, nonyl alcohol, dodecyl alcohol, and the like. Examples of suitable phenols are phenol, amyl phenol, octyl phenol, nonyl phenol, dodecylphenol, alkylated naphthols, and the like. Frequently, mixtures of alkanols are employed, such as mixtures of isopropanol-amyl alcohol, isobutanol-amyl alcohol, isobutanol-n-hexanol, and the like. Likewise, mixtures of phenols can be employed, such as mixtures of nonyl phenol with o-cresol, and the like. Mixtures of alkanols and phenols can also be used to give mixed alkyl/aryl dithiophosphoric acids.

In the preparation of the dihydrocarbyl-substituted dithiophosphoric acid any conventional method can be used, such as for example the preparations described in U.S. Pat. Nos. 2,552,570; 2,579,038; and 2,689,220. By way of illustration, in the preparation of a dialkaryl-substituted dithiophosphoric acid, about 2 moles of $P_2S_5$ may be added to about 8 moles of alkylphenol, e.g. nonylphenol, dodecylphenol, at 135°–140° C, at such a rate as to maintain $H_2S$ evolution under control. The temperature is then maintained until the reaction is essentially complete. During the last 15 minutes of the reaction period the mixture is preferably blown with nitrogen.

Since the present invention is applicable to the preparation of the zinc salt of a dihydrocarbyl-substituted dithiophosphoric acid prepared by any method, the preparation of the acid is not part of the present invention, and therefore, it is not to be restricted to any conditions for the preparation of such dithiophosphoric acid which may be described herein, which are given by way of illustration only.

The zinc salt of the dihydrocarbyldithiophosphoric acid may be prepared, in accordance with a highly preferred embodiment of the present invention, by reacting such dithiophosphoric acid with at least a stoichiometric amount, preferably from about 5% to about 20% in excess of the stoichiometric amount, of zinc oxide in a mineral process oil which has been treated with $NO_2$. Neutralization with the zinc oxide may be carried out at temperatures of from about 20° C to about 150° C, and preferably about 50°–100° C. During the reaction the mixture can be blown with nitrogen or other inert gases to remove water formed during the neutralization step, or the neutralization reaction can be conducted under vacuum to aid in such removal.

Mineral oils which can be used in the process include any normally liquid mineral oil. The preferred oils are petroleum-derived oils having a viscosity range of about 100 to 200 SSU at 100° F.

The mineral oils may be treated with $NO_2$ by directly injecting with $NO_2$ preferably in gaseous form. This can be conducted over a broad temperature range, such as from about 0° C or colder to in excess of 200° C. Good results have been achieved by conducting the $NO_2$ treatment under ambient conditions of about 20°–35° C.

The $NO_2$ treatment is conducted until the oil acts as a promotor for the neutralization reaction with zinc oxide. The extent of $NO_2$ treatment required to accomplish this can be readily determined experimentally. In general, it has been found that the oil acts as a promotor after sufficient $NO_2$ has been injected to lower the pH of the oil to below about 4.0, and preferably into the range of about 2.5–3.9. Analysis of the process oil at this time has shown it to contain about 0.2–0.3 weight percent nitrogen. Additional $NO_2$ can be injected to obtain nitrogen contents in excess of 0.3 up to about 0.5 weight percent or higher, but this is unnecessary because good results are usually obtained even with the smaller amounts of $NO_2$.

The amount of $NO_2$-treated mineral oil used in the neutralization reaction is not critical so long as there is sufficient amount to promote the reaction rate. In practice, an amount of from about 15 to 70 parts by weight of $NO_2$-treated oil per each 100 parts of dihydrocarbyldithiophosphoric acid is useful.

After the mineral oil has been treated with $NO_2$ the required amount of zinc oxide is added to it and then the dihydrocarbyldithiophoric acid, generally in a mineral oil diluent, is added. The neutralization reaction can be conducted in a temperature range of about 20°–150° C. In a more preferred embodiment the initial phase of the neutralization reaction is conducted at a lower temperature of about 50°–80° C and the latter phase of the reaction at a higher temperature of about 80°–110° C. During the neutralization it is preferred to apply vacuum to remove water and any other volatile material.

As mentioned previously, a slight stoichiometric excess of zinc oxide is preferred. The reaction with zinc oxide should preferably be conducted until the pH of the product rises above about 5.0, more preferably above about 5.8. Depending upon reaction conditions, this is generally accomplished in about 2–8 hours.

After the neutralization reaction with zinc oxide the reaction mixture may be filtered to remove any unreacted zinc oxide or other solids. A further advantage of the present process is that it may facilitate the filtration. In practice, it has been found that the filtration may proceed at about three times the rate observed with other known processes.

Zinc dihydrocarbyldithiophosphates, especially the zinc dialkaryldithiophosphates, made according to the present process may have a pH substantially above that obtained without the $NO_2$ treatment of the process oil. Thus zinc dialkaryldithiophosphates made according to the present process may have a pH above about 5.0. In practice, they may have a pH as high as about 5.8 or even higher.

The pH referred to is the apparent pH and is measured by dissolving a small amount (approx. 1.5 g) of the additive in a neutral polar solvent (e.g. 20 ml water + 40 ml diethyl ether + 40 ml. ethanol) and reading the pH of the solution.

It is to be understood that the present invention also includes zinc dihydrocarbyldithiophosphates when prepared by the process of the invention, such products being useful, for example, as antioxidants and anti-wear additives in lubricants. In yet another aspect the present invention therefore includes a lubricating composition containing a major amount of lubricating oil and a minor amount, for example, from 0.1% to 10%, preferably from 0.5% to 5% by weight based on the total weight of the lubricating composition, of a product prepared by the process of the present invention.

It is to be understood that lubricating compositions containing compounds prepared according to the process of the present invention may also contain conventional lubricating composition additives such as one or more additional antioxidants and anti-wear additives, corrosion inhibitors, detergents, dispersants, viscosity index improvers, extreme pressure additives or any combination thereof.

The following example illustrates the process of this invention. All parts are by weight unless otherwise stated.

EXAMPLE 1

Preparation of Dialkaryldithiophosphoric Acid

In a reaction vessel, 504.5 parts of $P_2S_5$ were reacted with 2000 parts of nonylphenol to produce dinonylphenyl dithiophosphoric acid.

$NO_2$ Treatment of Process Oil

To a reaction vessel charge 700 parts of process oil (neutral mineral oil 100 SSU at 100° F). While stirring at 20°–25° C, inject gaseous $NO_2$ into the oil until 5.5 parts are absorbed.

Neutralization with Zinc Oxide

In a reaction vessel place 66.5 parts of the above $NO_2$-treated process oil and 10.8 parts of zinc oxide. Evacuate the vessel to 26 inches Hg vacuum. While stirring, heat the mixture to 65° C and add 200 parts of the above dinonylphenyl dithiophosphoric acid diluted with a 100 SSU at 100° F. neutral mineral oil to give an observed equivalent weight of 838.3 g/equivalent, over a 15 minute period at 65°–70° C. Stir the mixture at 65°–70° C for an additional 90 minutes and then heat to 100° C while maintaining vacuum. Continue stirring at 100°–105° C for 150 minutes. At the end of this period release vacuum and filter the product. The resultant product is a clear bright oil solution of zinc dinonylphenyl dithiophosphate(2.86% Zn, 2.71% P, 6.58% S, pH 6.1), which is useful as an antioxidant-antiwear additive in crankcase lubricating oils.

Other dihydrocarbyldithiophosphoric acids can be used in the above example by substituting other phenols or alkanols for the nonyl phenol. Likewise, variations in the operating procedure made in accordance with the previous description can be employed with good results.

The zinc dihydrocarbyldithiophosphates are generally used in combination with other conventional additives, such as calcium alkaryl sulphonates, magnesium alkaryl sulphonates, barium phenates, phosphosulphurized polyolefins, sulphurized isobutylene, and the like.

We claim:

1. In the process of making an oil solution of a zinc dihydrocarbyl dithiophosphates by reacting zinc oxide with a dihydrocarbyldithiophosphoric acid in a mineral oil reaction medium, the improvement comprising reacting said mineral oil with nitrogen dioxide in an amount sufficient to promote the reaction of said zinc oxide with said dihydrocarbyldithiophosphoric acid.

2. The improved process of claim 1 wherein said dihydrocarbyldithiophosphoric acid is a dialkaryldithiophosphoric acid.

3. The improved process of claim 2 wherein said mineral oil is reacted with nitrogen dioxide in an amount sufficient to lower its pH to below about 4.0 prior to use as said reaction medium.

4. The improved process of claim 3 wherein said dialkaryldithiophosphoric acid is dinonylphenyldithiophosphoric acid.

* * * * *